United States Patent
Bonderer

(10) Patent No.: US 11,649,345 B2
(45) Date of Patent: *May 16, 2023

(54) BURN-OUT DENTAL MODELLING MATERIAL

(71) Applicant: Ivoclar Vivadent AG, Schaan (LI)

(72) Inventor: Lorenz Josef Bonderer, Sargans (CH)

(73) Assignee: Ivoclar Vivadent AG, Schaan (LI)

( * ) Notice: Subject to any disclaimer, the term of this patent is extended or adjusted under 35 U.S.C. 154(b) by 95 days.

This patent is subject to a terminal disclaimer.

(21) Appl. No.: 17/234,937

(22) Filed: Apr. 20, 2021

(65) Prior Publication Data

US 2021/0238403 A1 Aug. 5, 2021

Related U.S. Application Data

(63) Continuation of application No. 16/467,220, filed as application No. PCT/EP2017/081802 on Dec. 7, 2017, now Pat. No. 11,021,600.

(30) Foreign Application Priority Data

Dec. 15, 2016 (EP) .................................... 16204527

(51) Int. Cl.
| | |
|---|---|
| *C08L 33/04* | (2006.01) |
| *A61K 6/887* | (2020.01) |
| *A61K 6/60* | (2020.01) |
| *C08K 5/06* | (2006.01) |
| *C08K 5/08* | (2006.01) |
| *C08K 5/101* | (2006.01) |
| *C08K 5/56* | (2006.01) |

(52) U.S. Cl.
CPC ............... *C08L 33/04* (2013.01); *A61K 6/60* (2020.01); *A61K 6/887* (2020.01); *C08K 5/06* (2013.01); *C08K 5/08* (2013.01); *C08K 5/101* (2013.01); *C08K 5/56* (2013.01)

(58) Field of Classification Search
CPC ...................................................... A61K 6/887
See application file for complete search history.

(56) References Cited

U.S. PATENT DOCUMENTS

| | | | |
|---|---|---|---|
| 4,613,560 A | 9/1986 | Dueber et al. | |
| 6,262,159 B1 | 7/2001 | Stefan et al. | |
| 2007/0207094 A1* | 9/2007 | Oxman | A61K 6/887 424/49 |
| 2009/0030102 A1* | 1/2009 | Nelles | C08J 3/28 522/43 |
| 2010/0029801 A1* | 2/2010 | Moszner | G03F 7/0037 522/167 |

OTHER PUBLICATIONS

Gebhardt, A., "Vision Rapid Prototyping," University of Applied Sciences/Aachen, DKG 83 (2006) No. 13.
International Preliminary Report on Patentability of PCT/EP2017/081802, dated Jun. 18, 2019, 8 pages.
Gebhardt, A., "Additive Manufacturing Systems for Rapid Prototyping, Direct Tooling and Direct Manufacturing," Generative Gertigungverfahren, 3rd Edition, Carl Hanser Verlag, Munich, Germany, 2007.
Beil, A., "Production of Micro-Components by Stereolithography," Düsseldorf, Germany, VDI, Series 2, No. 617, 2002.

* cited by examiner

*Primary Examiner* — Michael F Pepitone
(74) *Attorney, Agent, or Firm* — Ann M. Knab; Thad McMurray

(57) ABSTRACT

Modelling material which contains (a) at least one radically polymerizable monomer, (b) at least one initiator for the radical polymerization and (c) at least one inert component. The inert component (c) is selected from phthalates, polyethylene glycols (PEG), polypropylene glycols (PPG), PEG-PPG copolymers, glycerol derivatives, ethoxylated or propoxylated glycerol, ethylenediamine tetrakispropoxylates and ethylenediamine tetrakisethoxylates. The material is suitable in particular for the production of models of dental restorations for investment casting processes.

20 Claims, 16 Drawing Sheets

BURN-OUT DENTAL MODELLING MATERIAL

CROSS-REFERENCE TO RELATED APPLICATIONS

This application claims priority to and is a Continuation application of U.S. application Ser. No. 16/467,220, filed Jun. 6, 2019, now U.S. Pat. No. 11,021,600, which is the National Stage application of International patent application No. PCT/EP2017/081802 filed on Dec. 7, 2017, which claims priority to European patent application No. 16204527.2 filed on Dec. 15, 2016, all the disclosures of which are incorporated herein by reference in their entirety.

FIELD OF THE INVENTION

The present invention relates to materials which are suitable in particular for the production of dental models for investment casting processes. Investment casting processes are used for the production of shaped parts which require a high degree of accuracy and thus in particular for the production of dental restorations, such as inlays, onlays, veneers, crowns, bridges and frameworks.

BACKGROUND OF THE INVENTION

For the production of dental restorations according to the conventional lost-wax technique, a wax model (wax-up) is shaped, invested in an investment material and heated up in a furnace after this has set. The wax melts and flows out of the mould. The mould is then heated further, whereby wax residues burn. In this way, a negative of the wax model is obtained into which an alloy or a ceramic material is then poured. The cast object is then again a positive which is exactly the same as the wax model.

The production of the wax model can be carried out in different ways. In the case of manual modelling, a model of the tooth restoration is built up by the dental technician in layers on a plaster model using a special dental wax. The waxes soften on warming and, after melting, flow out of the investment material, normally without causing cracks. This process is still the gold standard with regard to the quality of cast and pressed objects.

In newer processes, the wax model is milled out of wax discs or blocks using CAD/CAM processes. The waxes used here require a compromise between good milling qualities and ability to burn out. The products which are commercially available today for the most part meet both requirements sufficiently well. These waxes also soften on warming and, after melting, flow out of the investment material without causing cracks.

Wax models are relatively delicate with the result that, increasingly, alternative materials are used for the production of models. In the case of CAD/CAM processes, plastic discs and blocks as well as plastic-wax hybrid discs are used, for example.

In the case of manual modelling, curable resins, which can be cured cold by mixing two components, thermally or preferably by light, are used as alternatives to waxes. These materials contain relatively large quantities of non-meltable duromers.

Recently, so-called additive processes are increasingly being used for the production of models. By this is meant manufacturing processes in which three-dimensional models or components are produced from computer-aided design data (CAD data) (A. Gebhardt, Vision of Rapid Prototyping, DGK Report 83 (2006) 7-12). These are processes such as e.g. stereolithography (SL), selective laser sintering (SLS), 3D printing, fused deposition modelling (FDM), ink-jet printing (IJP), 3D plotting, multi-jet modelling (MJM), solid freeform fabrication (SFF), laminated object manufacturing (LOM), laser powder forming (LPF), with which models, components or shaped parts can be produced cost-effectively even on a small scale (A. Gebhardt, Generative Fertigungsverfahren [Additive Manufacturing Processes], 3rd ed., Carl Hanser Verlag, Munich 2007, 77 et seq.). In the case of stereolithography, a shaped part is built up in layers from a liquid and curable monomer resin on the basis of CAD data (A. Beil, Fertigung von Mikro-Bauteilen mittels Stereolithographie [Manufacture of micro-components using stereolithography], Dusseldorf 2002, VDI-Verlag 3 et seq.). Additive processes are often covered by the term "Rapid Prototyping" (RP).

A disadvantage of the materials used as alternatives to waxes is their melting behaviour. Pure waxes first of all soften on warming, then melt and subsequently flow out of the mould. During the thermally caused expansion, they do not therefore exert large forces on the investment material. The alternative materials do not exhibit this melting behaviour. They expand thermally during the setting/curing of the investment material and the temperature rise associated therewith as well as during the subsequent heating, however do not flow out of the mould but are primarily removed therefrom by thermal decomposition. During the expansion, they therefore exert pressure on the investment material, which leads to stresses and, in particular in the case of large-volume dental restorations, to cracks in the negative mould, which result in pressing and casting defects and, in the case of larger cracks, also in faulty pressings or faulty castings.

It is known to add wax particles to curable materials. These are intended, during setting of the investment material or during burn out in the furnace, to melt and thus to create space for the expanding material. However, often the molten wax cannot escape or can only escape with difficulty because it is enclosed by the polymerized material and because the diffusion coefficient of the molten wax molecules through the polymer matrix is only very small. In the least favourable case, the large increase in volume of the waxes on melting actually increases the thermal expansion of the model instead of reducing it.

SUMMARY OF THE INVENTION

The object of the invention is to provide materials for modelling dental prostheses which do not exhibit the disadvantages named above. They are intended to enable the production of models, in particular by stereolithographic processes, which can be removed without the formation of cracks after the investment material has set, with the result that fault-free moulds and restorations are obtained.

This object is achieved according to the invention by radically polymerizable compositions which contain (a) at least one radically polymerizable monomer, (b) at least one initiator for the radical polymerization and (c) at least one inert component. Component (c) is an organic compound.

BRIEF DESCRIPTION OF THE DRAWINGS

The invention is explained in more detail below by means of figures and embodiment examples.

FIG. 13, material V2; FIG. 14, material V3). The bridge frameworks exhibit clearly visible pressing defects.

DETAILED DESCRIPTION

Figure 1:
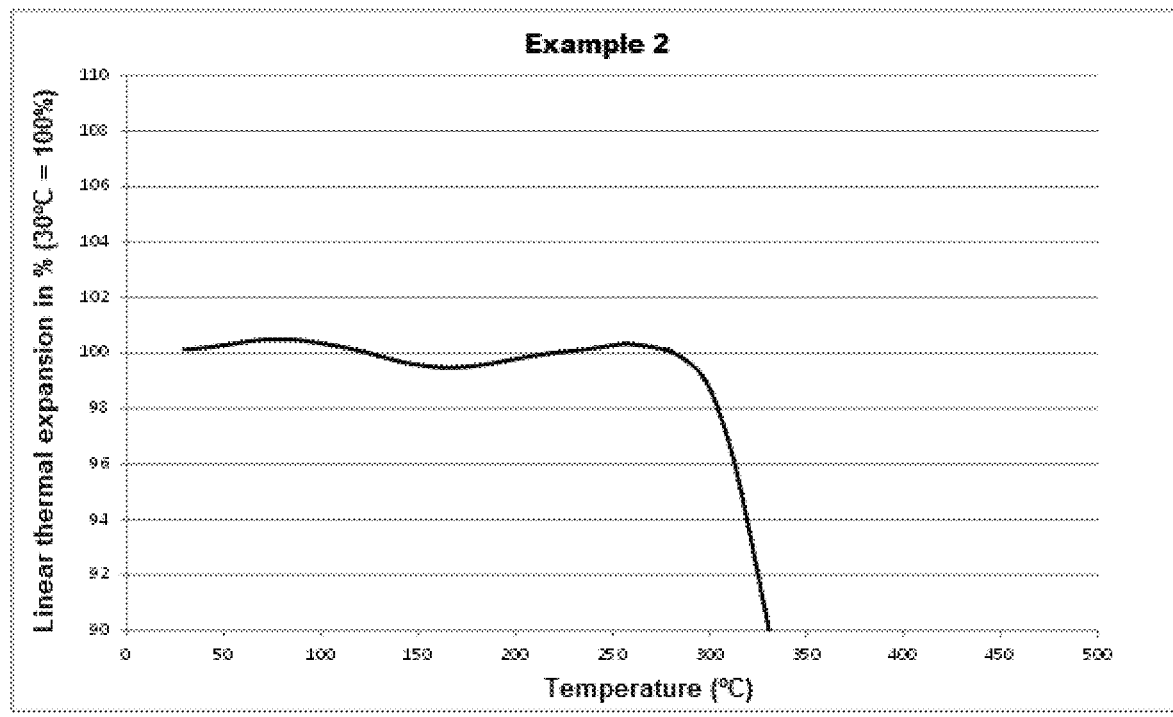
FIG. 1 shows the thermal expansion curve of the material according to the invention from Example 2, measured on cylinders with a 6 mm diameter and a height of 6 mm. The measurement was carried out using a Q400 measuring device from TA Instruments with a macro-expansion probe.
Figure 2:
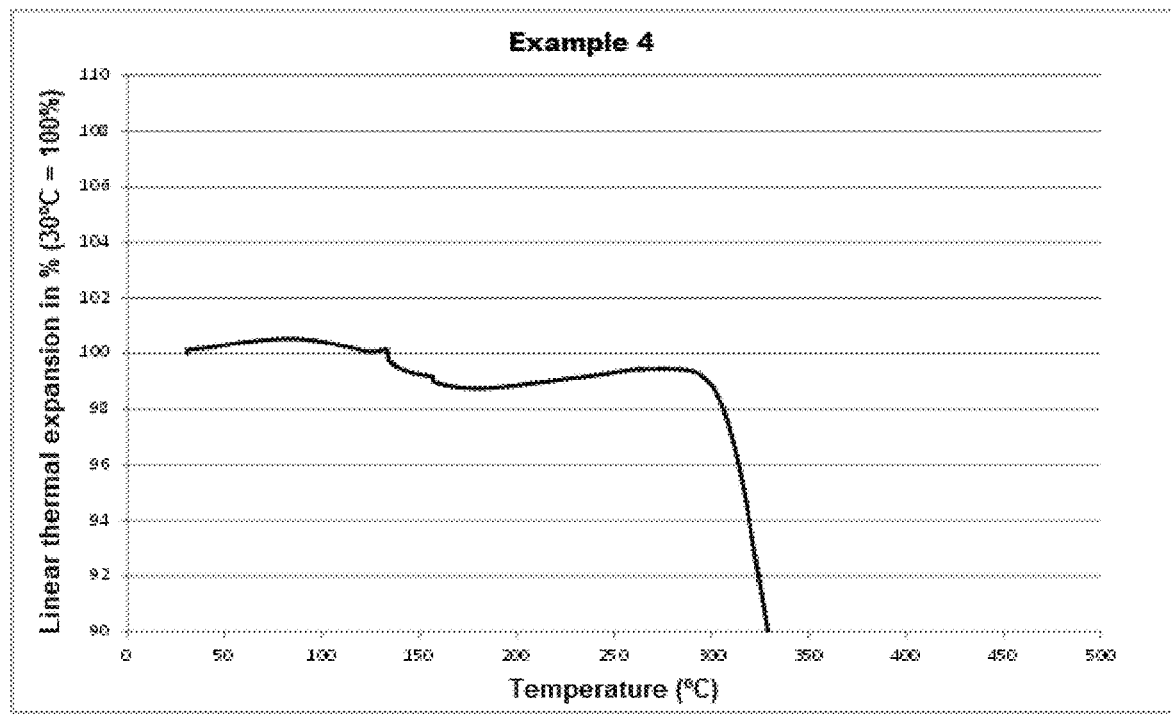
FIG. 2 shows the thermal expansion curve of the material according to the invention from Example 4.
Figure 3:
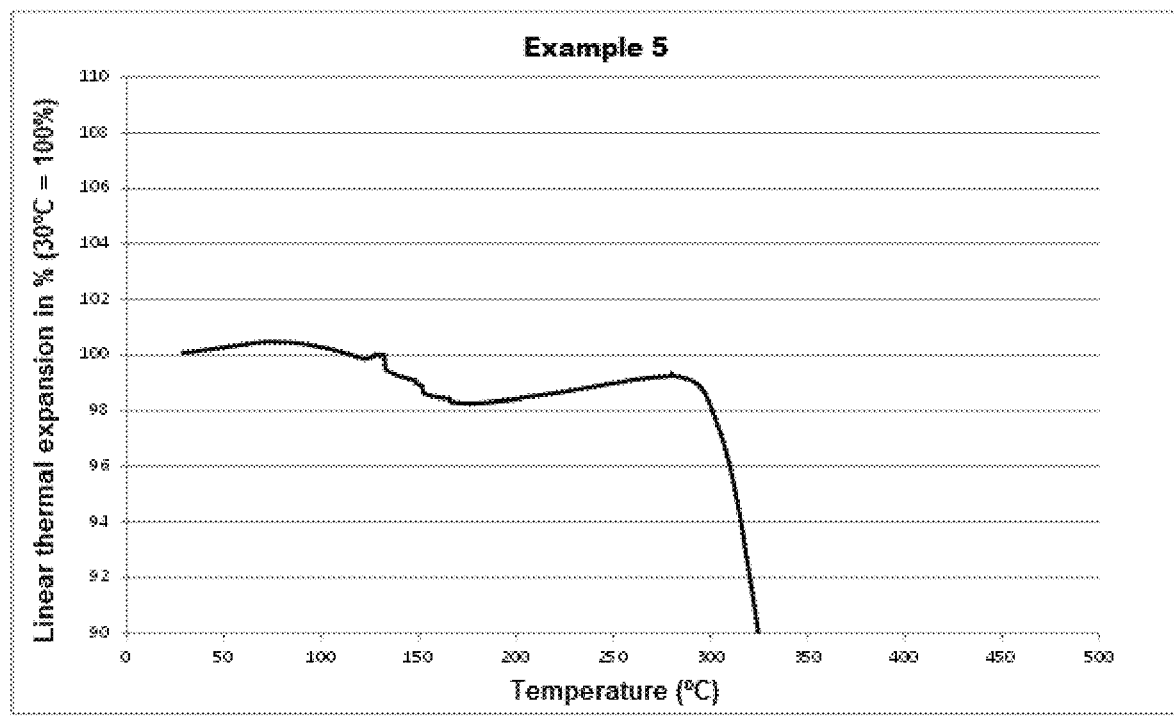
FIG. 3 shows the thermal expansion curve of the material according to the invention from Example 5.
Figure 4:
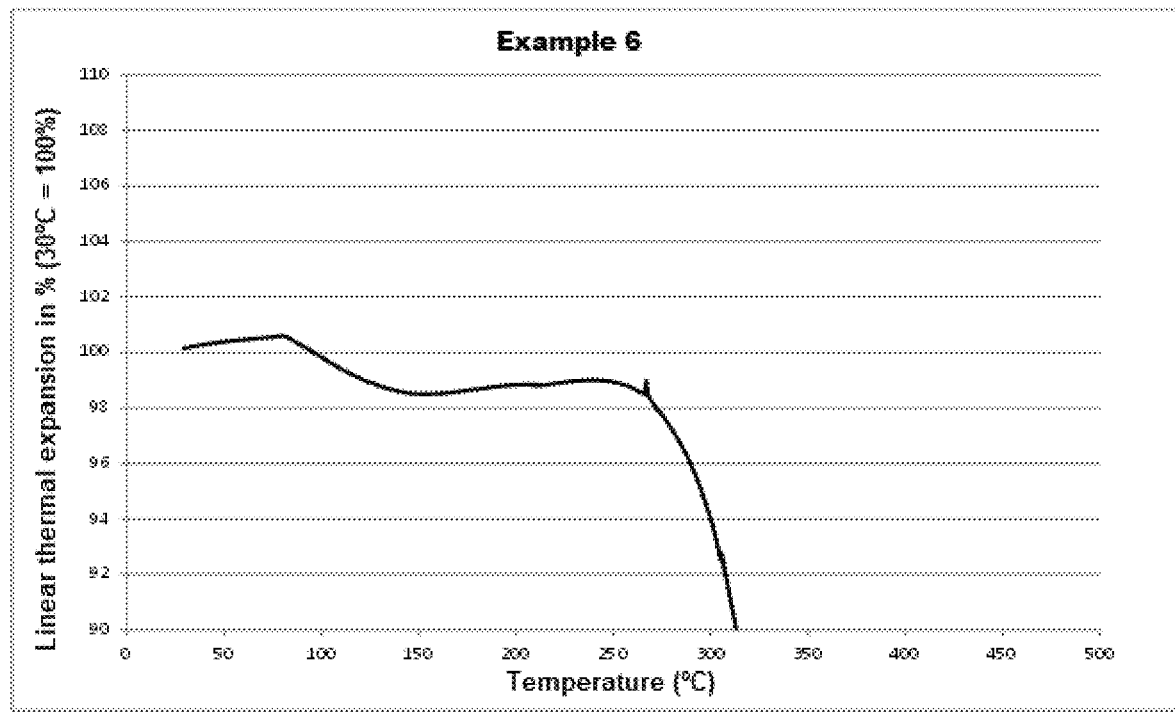
FIG. 4 shows the thermal expansion curve of the material according to the invention from Example 6.

The compositions according to the invention are characterized in that, as inert component (c), they contain one or more phthalates, polyethylene glycols (PEG), polypropylene glycols (PPG), PEG-PPG copolymers, glycerol derivatives, i.e. in particular ethoxylated or propoxylated glycerol, ethylenediamine tetrakispropoxylates and/or ethylenediamine tetrakisethoxylates. In all cases, the propoxylated compounds are preferred over the ethoxylated compounds because ethoxylates tend, at higher molecular weights, to become solid and then require higher processing temperatures.

Component (c) can be solid at room temperature as long as it does not precipitate out of the monomer used or out of the monomer mixture at the processing temperature. However, substances are preferred which are pasty and in particular liquid at room temperature. The consistency of component (c) can be adjusted, for example, by the proportion of PPG groups, e.g. by mixing propoxylated and ethoxylated compounds or by increasing the proportion of PPG groups within the molecule, e.g. in the case of PEG-PPG copolymers. The proportion of PPG groups is preferably so high that the component is liquid or pasty, particularly preferably so high that the pour point is lower than the processing temperature.

According to DIN 51597, for a liquid product, the pour point refers to the temperature at which, on cooling, it only just flows. The setting point according to DIN 51583 refers to the temperature at which the previously liquid product solidifies. The pour point is determined in accordance with DIN 51597/ISO 3016.

Component (c) preferably has a molecular weight of 1000 to 10,000 g/mol, particularly preferably 1000 to 5000 g/mol. Polyethylene glycols (PEG) preferably have a molecular weight of 1000 to 5000 g/mol, particularly preferably 1000 to 3000 g/mol, polypropylene glycols (PPG) of 1000 to 4000 g/mol, particularly preferably 1500 to 3000 g/mol and in particular 2000 g/mol, PEG-PPG copolymers of 1000 to 10,000 g/mol, preferably 1500 to 5000 g/mol and in particular 2000 to 4000 g/mol.

The ethylenediamine tetrakispropoxylates and -ethoxylates preferably have a molecular weight of 1000 to 10,000 g/mol, in particular of 1000 to 5000 g/mol, wherein ethylenediamine tetrakispropoxylates and mixtures of ethylenediamine tetrakisethoxylates and -propoxylates are preferred to the ethylenediamine tetrakisethoxylates.

Unless otherwise stated, here the molar mass of polymers in all cases is the molar mass Mη determined by viscometry (viscosity average).

Particularly preferred components (c) are polypropylene glycols (PPG), in particular PPG with a molecular weight of 1000 to 4000 g/mol, preferably 1500 to 3000 g/mol, co-PEG-PPG with a molecular weight of 1000 to 10,000 g/mol, preferably 1500 to 5000 g/mol and quite particularly polypropylene glycol with a molecular weight of approx. 2000 g/mol.

Mixtures of the named substances can also be used advantageously. In addition to the named components, these mixtures can also contain compounds with a molecular weight of less than 1000 g/mol in a lesser quantity.

Terminal —OH groups of the named compounds can be esterified or etherified, for example with methyl, ethyl, propyl or iso-propyl groups or formate, acetate, propionate or iso-propionate groups.

Under standard conditions (20° C., 1013 mbar), component (c) is liquid or solid and preferably has a pour point of above −150° C., particularly preferably of above −100° C. and quite particularly preferably of above −50° C.

Component (c) preferably has a boiling point of above 80° C., preferably above 120° C., particularly preferably above 150° C. Components which do not boil under standard pressure without decomposition preferably have a thermal decomposition temperature of above 120° C., preferably above 135° C., particularly preferably above 150° C. The relatively high boiling and decomposition temperature ensures that component (c) is also solid or liquid under conditions of use and, for example, does not evaporate when the investment material is printed or sets. Compounds with a maximum boiling temperature of 350° C. and/or a maximum decomposition temperature of 500° C. are preferred.

Component (c) is chemically inert, this means that it does not react or does not markedly react with the other components of the material under storage conditions and conditions of use. In particular, component (c) does not contain any radically polymerizable groups and therefore does not copolymerize with the monomer (a). It is homogeneously miscible with component (a), and mixtures of (a) and (c) are stable at the processing temperature, i.e. no phase separation takes place, in particular component (c) does not precipitate out or crystallize out during processing. The processing of the materials according to the invention, i.e. the production of models, for example by stereolithographic printing, preferably takes place at a temperature of 15 to 35° C., preferably 15 to 30° C. Materials are preferred that can be processed and stored at room temperature (20° C.) so that the materials do not additionally need to be warmed for processing or do not need to be cooled for storage.

Compounds which burn without residue in particular come into consideration as component (c). By this is meant substances which preferably form less than 0.1 wt.-% ash on burning. Compounds are preferred which burn on heating in an oxidizing atmosphere to a temperature of approx. 850° C.

The compositions according to the invention contain, as component (a), at least one radically polymerizable monomer and, as component (b), at least one initiator for the radical polymerization. They are preferably in the form of a homogeneous mixture of components (a), (b), (c) and optional constituents that may be present. They can be cured thermally, via a two-component initiator system or photochemically, depending on the initiator used. Compositions which contain a photoinitiator are preferred.

According to the invention, materials for the production of models by manual modelling are preferred, by additive manufacturing processes are particularly preferred and by stereolithography are quite particularly preferred. By a model is meant here in particular the desired positive mould for investment casting processes. Although, unlike in the conventional lost-wax technique, the model is primarily removed from the mould by burning out after the investment material has set, the process here is referred to as investment casting. The material according to the invention is suitable in particular for the production of models for manufacturing dental restorations.

The modelling materials according to the invention are characterized by a relatively low maximum linear thermal expansion. This is preferably below 1.5%, preferably below 1%, particularly preferably below 0.7%. The linear thermal expansion is measured in the temperature range from 30° C. to 800° C., wherein most materials already start to decompose before 800° C. is reached. The decomposition manifests itself in shrinkage of the measurement bodies.

It is particularly advantageous for the maximum expansion to be reached at a temperature of below 150° C., preferably below 120° C., particularly preferably below 100° C. and quite particularly preferably below 90° C. In contrast, commercially available burn-out SL resins typically have a maximum thermal expansion of 2% or more which is, in addition, only reached at relatively high temperatures.

Figure 5:
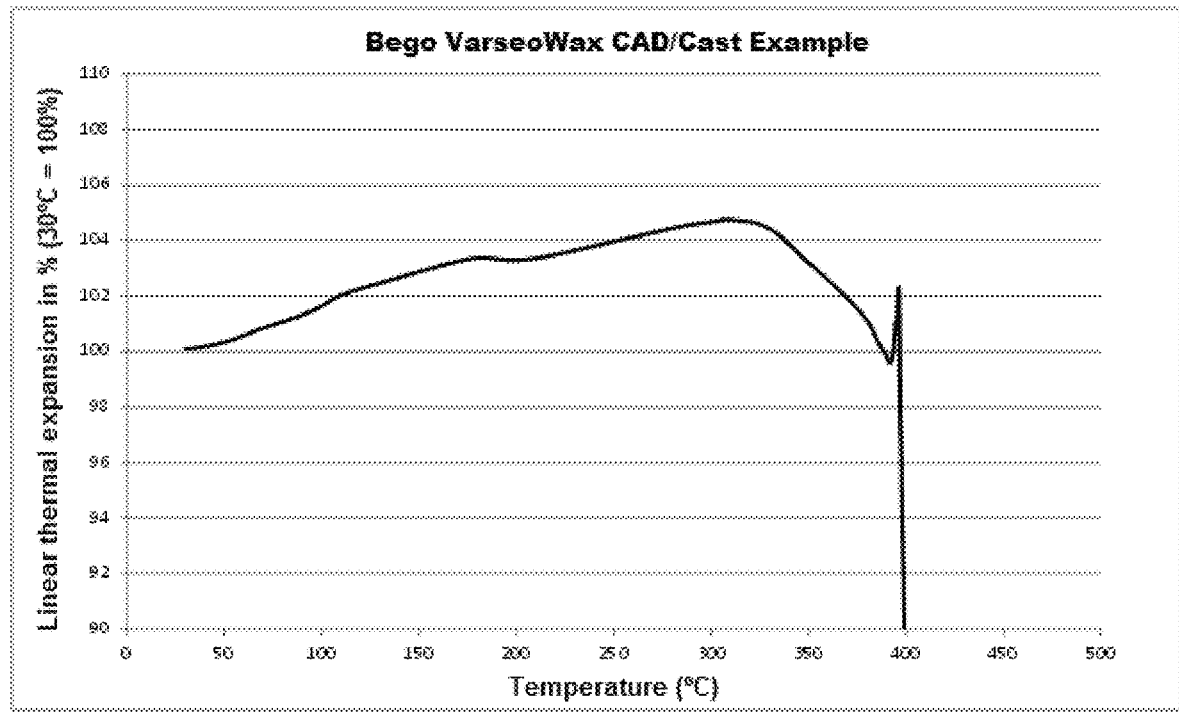
FIGS. 5 and 6 show the expansion curves of materials customary in the trade according to the state of the art.

FIG. 5 shows the thermal expansion behaviour of a conventional material. Conventional materials expand thermally on warming and the volume increases continuously. Above a particular temperature, the materials start to decompose. The decomposition manifests itself in a reduction in volume. The decomposition temperature is material-dependent and, for most organic materials, is above 300° C.

On warming, most materials according to the invention first also exhibit a slight expansion, but this turns out to be considerably smaller than in the case of conventional materials (FIGS. 1-4). The expansion curves already fall again significantly before the decomposition temperature is reached. Although a slight rise in the curves is sometimes observed again at higher temperatures, this turns out to be comparatively small. Overall, the materials according to the invention expand over the entire temperature range up to decomposition considerably less than known materials.

The expansion curves pass through a maximum. Here, this maximum of the thermal expansion is referred to as maximum linear thermal expansion.

The thermal expansion is preferably determined on cylinders with a 6 mm diameter and a height of 6 mm in the temperature range of from 30° C. to 800° C. at a heating rate of 5 K/min in an air atmosphere. The measuring probe is applied to the sample with a contact force of 0.1 N. The linear expansion of the cylinders during heating up and thermal decomposition is measured. The measurement can take place e.g. using a Q400 thermomechanical analyzer (TMA) from TA Instruments with a macro-expansion probe. The length of the cylinder at 30° C. is taken as the original length, i.e. 0% expansion.

The thermal expansion behaviour of the materials according to the invention at the least greatly reduces the risk of defects such as cracks or even the destruction of the mould during burn-out and for the most part eliminates it completely. In this way, the materials according to the invention produce crack-free moulds with a high degree of accuracy and precision.

The materials according to the invention preferably contain, as radically polymerizable monomer (a), at least one (meth)acrylate and/or (meth)acrylamide, preferably one or more mono- or multifunctional (meth)acrylates or a mixture thereof. Materials which contain at least one multifunctional (meth)acrylate or a mixture of mono- and multifunctional (meth)acrylates as radically polymerizable monomer are particularly preferred. By monofunctional (meth)acrylates is meant compounds with one, by polyfunctional (meth)acrylates is meant compounds with two or more, preferably 2 to 6, radically polymerizable groups. In all cases, methacrylates are preferred to acrylates.

Particularly suitable mono- or multifunctional (meth)acrylates are methyl, ethyl, 2-hydroxyethyl, butyl, benzyl, tetrahydrofurfuryl or isobornyl (meth)acrylate, p-cumyl-phenoxyethylene glycol methacrylate (CMP-1E), bisphenol A di(meth)acrylate, bis-G(M)A (an addition product of (meth)acrylic acid and bisphenol A diglycidyl ether), ethoxylated or propoxylated bisphenol A di(meth)acrylate, such as e.g. bisphenol A di(meth)acrylate with 3 (SR-348c=methacrylate; SR-349=acrylate, Sartomer) or 2 ethoxy groups (SR-348L=methacrylate, Sartomer), 2,2-bis[4-(2-(meth)acryloxypropoxy)phenyl]propane, UD(M)A (an addition product of 2-hydroxyethyl (meth)acrylate and 2,2,4- or 2,4,4-trimethylhexamethylene-1,6-diisocyanate), di-, tri-, tetra-, penta-, hexa- or heptaethylene glycol di(meth)acrylate, di-, tri-, tetra-, penta-, hexa- or heptapropylene glycol di(meth)acrylate, trimethylolpropane tri(meth)acrylate, ethoxylated or propoxylated trimethylolpropane tri (meth)acrylate, e.g. 3 times propoxylated trimethylolpropane triacrylate (Sartomer SR-492) and tripropylene glycol diacrylate, pentaerythritol tetra(meth)acrylate, as well as glycerol di- and tri(meth)acrylate, 1,4-butanediol di(meth)acrylate, 1,10-decanediol di(meth)acrylate ($D_3MA$), 1,12-dodecanediol di(meth)acrylate or oligomeric polyether, polyester, epoxy or urethane (meth)acrylates and tricyclodecane dimethanol di(meth)acrylate.

Particularly preferred are mono- and in particular di- and trifunctional acrylates and methacrylates with a molecular weight of <1000 g/mol, such as e.g. 2-phenoxyethyl (meth)acrylate, aliphatic urethane diacrylates, phthalic acid-HEA ester (Photomer 4173), pyromellitic acid-di-HEA ester (HEA=2-hydroxyethyl acrylate), bis-G(M)A (an addition product of (meth)acrylic acid and bisphenol A diglycidyl ether), 2,2-bis[4-(2-(meth)acryloxypropoxy)phenyl]propane, UD(M)A, triethylene glycol di(meth)acrylate (TEGD (M)A) and 2-phenoxyethyl (meth)acrylate (acrylate SR339C Sartomer/Arkema). These monomers are characterized by a high reactivity, a high double bond conversion, good mechanical properties, a low polymerization shrinkage and a relatively low viscosity. Quite particularly preferred are those materials which contain, as component (a), UDMA, TEGDMA, bis-GMA (addition product of methacrylic acid and bisphenol A diglycidyl ether) or 2-phenoxyethyl acrylate (SR339C, Sartomer/Arkema), a mixture of UDMA, TEGDMA and 2-phenoxyethyl acrylate or preferably UDMA, TEGDMA and bis-GMA and in particular a mixture of UDMA and TEGDMA.

The properties of the materials before and after the curing can be influenced by a targeted combination of monomers.

Mixtures of monofunctional and difunctional monomers are characterized by a relatively low viscosity and reactivity of the resin mixture, wherein viscosity and reactivity decrease with the content of monofunctional monomers. A monofunctional monomer content ensures a lower rigidity of the models obtained by curing the materials. Mixtures of difunctional and trifunctional monomers have a higher reactivity, wherein the reactivity increases with the content of trifunctional monomers. The trifunctional monomer content causes a higher brittleness. Reactivity and viscosity of the resin mixture and also the polymerization shrinkage are furthermore determined by the molar mass of the monomers, wherein the polymerization shrinkage decreases with increasing molar mass, while the viscosity increases.

Preferred photoinitiators (b) for initiating the radical photopolymerization are benzophenone, benzoin and derivatives thereof or α-diketones or derivatives thereof, such as 9,10-phenanthrenequinone, 1-phenyl-propane-1,2-dione, diacetyl or 4,4'-dichlorobenzil. Camphorquinone (CQ) and 2,2-dimethoxy-2-phenyl-acetophenone are particularly preferably used, and α-diketones in combination with amines as reducing agent, such as e.g. 4-(dimethylamino)benzoic acid ester (EDMAB), N,N-dimethylaminoethyl methacrylate, N,N-dimethyl-sym.-xylidine or triethanolamine, are quite particularly preferably used. Further preferred are diethylthioxanthene (DETX, CAS 82799-44-8) and isopropylthioxanthone (ITX, CAS 75081-21-9), both in each case preferably in combination with ethyl 4-(dimethylamino)benzoate (EMBO, CAS No. 10287-53-3). Likewise preferred are [1-(4-phenylsulfanylbenzoyl)heptylidenamino] benzoate (Irgacure OXE 01) and [1[9-ethyl-6-(2-methylbenzoyl)carbazol-3-yl]ethylidenamino]acetate (Irgacure OXE 02).

Particularly preferred photoinitiators are furthermore Norrish type I photoinitiators, above all monoacyl- or bisacylphosphine oxides, and in particular monoacyltrialkyl- or diacyldialkylgermanium compounds, such as e.g. benzoyltrimethylgermanium, dibenzoyldiethylgermanium or bis(4-methoxybenzoyl)diethylgermanium (MBDEGe). Advantageously, mixtures of the different photoinitiators can also be used, such as e.g. bis(4-methoxybenzoyl)diethylgermanium in combination with camphorquinone and 4-dimethylaminobenzoic acid ethyl ester.

Quite particularly preferred are camphorquinone (CAS No. 10373-78-1) in combination with ethyl 4-(dimethylamino)benzoate (EMBO, CAS No. 10287-53-3) as well as phenylbis(2,4,6-trimethylbenzoyl)phosphine oxide (Irgacure 819, CAS 162881-26-7), diphenyl(2,4,6-trimethylbenzoyl)phosphine oxide (TPO, CAS No. 75980-60-8), 2-benzyl-2-(dimethylamino)-4'-morpholinobutyrophenone (Irgacure 369, CAS No. 119313-12-1), 1-butanone, 2-(dimethylamino)-2-(4-methylphenyl)methyl-1-4-(4-morpholinyl)phenyl (Irgacure 379, CAS No. 119344-86-4) and quite particularly bis(4-methoxybenzoyl)diethylgermanium (MBDEGe; Ivocerin).

According to the invention it was surprisingly found that, by coordinating the components, the thermal expansion behaviour of the materials can be adjusted in a targeted manner such that the maximum thermal expansion thereof is below 1.5%, preferably below 1%, particularly preferably below 0.7%, and, according to a particularly preferred embodiment, the maximum expansion is reached at a temperature of below 150° C., preferably below 120° C., particularly preferably below 100° C. and quite particularly preferably below 90° C.

It was found that the inert component (c) used according to the invention and in particular the named preferred components are homogeneously miscible with radically polymerizable monomers and in particular with acrylates and methacrylates and do not impair the polymerization of these monomers. During the stereolithographic processing of the compositions according to the invention in the liquid state, a high reactivity as well as short exposure and processing times can thereby be ensured.

According to the invention those materials are preferred in which component (a) contains UDMA, TEGDMA or a mixture thereof. Particularly preferred are materials in which component (a), in addition to UDMA and/or TEGDMA, contains at most 20 wt.-%, preferably at most 10 wt.-%, particularly preferably at most 5 wt.-% and quite particularly preferably less than 3 wt.-% or no further monomers, wherein the percentages relate to the total mass of component (a). Those materials are preferred in particular which contain, as component (a), UDMA or TEGDMA, particularly preferably a mixture of UDMA, TEGDMA and SR339C or of UDMA, TEGDMA and bis-GMA and in particular a mixture of UDMA and TEGDMA. As component (c), in each case PPG with a molar weight of 1000 to 4000 g/mol, preferably of 1500 to 3000 g/mol, quite particularly preferably 2000 g/mol is preferred.

In the case of the monomers preferred according to the invention, PPG with a molar weight of 2000 g/mol represents a good compromise. In the case of PEG-PPG-PEG, a molecular weight of approx. 3500 g/mol is advantageous. The temperature of the maximum thermal expansion is shifted towards higher values through the use of this component.

In addition to the above-named components, the materials according to the invention can advantageously contain further additives. For stereolithographic use, materials are preferred which contain at least one colorant and preferably also at least one polymerization inhibitor.

As colorant, organic dyes and pigments are preferred, in particular azo dyes, carbonyl dyes, cyanine dyes, azomethines and methines, phthalocyanines and dioxazines. Dyes are particularly preferred which are soluble in the materials, in particular azo dyes. Inorganic and in particular organic pigments which can be dispersed well in the materials are also suitable as colorant. Azo pigments and non-azo pigments are preferred. Those substances are preferably used as dyes which burn out without residue. For this reason, organic pigments are preferred to inorganic pigments. In the case where inorganic pigments are used, the quantity thereof is preferably calculated such that the ash content thereof after burn-out is below 0.1 wt.-%, relative to the total weight of the burn-out material.

The materials preferably contain at least one colorant which absorbs in the same wavelength range as the polymerization initiator. Colorants are particularly preferred which have an absorption maximum which corresponds to the wavelength of the light used for the curing. Colorants with an absorption maximum in the range of from 350 to 550 nm, preferably 380 to 480 nm, are particularly advantageous.

Colorants prevent the light used for the curing from penetrating too deep into the materials and thus have an advantageous effect on the precision of the components in the printing process, in particular in the case of stereolithographic processes. Moreover, colorants can also be added for aesthetic purposes.

The polymerization inhibitor(s) serve(s) as stabilizer to prevent a spontaneous polyreaction. The inhibitors or stabilizers improve the storage stability of the materials and also prevent an uncontrolled polyreaction in the stereolithographic tank. The inhibitors are preferably added in such a quantity that the materials are storage-stable for a period of approx. 2-3 years. The inhibitors are particularly preferably used in a quantity of 0.001 to 1.0 wt.-%, quite particularly preferably 0.001 to 0.20 wt.-%, in each case relative to the total mass of the material.

So-called aerobic inhibitors are preferred, in particular phenols such as hydroquinone monomethyl ether (MEHQ) or 2,6-di-tert-butyl-4-methyl-phenol (BHT), which are really effective only in the presence of oxygen and are preferably used in a concentration range from 100-2000 ppmw. Suitable anaerobic inhibitors are phenothiazine, 2,2, 6,6-tetramethyl-piperidine-1-oxyl radical (TEMPO), iodine and copper(I) iodide. These act even in low concentrations of preferably 10-200 ppmw even in the absence of oxygen. A polymerization does not take place until these additives have been consumed. It is advantageous to use a mixture of aerobic and anaerobic inhibitors.

Aerobic inhibitors are preferably used in a quantity of 0.001 to 0.50 wt.-% and anaerobic inhibitors in a quantity of 0.001 to 0.02 wt.-%, in each case relative to the total mass of the material. Preferred mixtures contain 0.005-0.10 wt.-% aerobic inhibitors and 0.001 to 0.02 wt.-% anaerobic inhibitors, likewise relative to the total mass of the material.

The modelling materials according to the invention can also contain particulate filler. Generally, organic particles are preferred as fillers, in particular fillers which burn without forming ash. The filler(s) preferably has(have) a particle size of less than 25 µm, preferably less than 10 µm and particularly preferably less than 5 µm. All of the particle sizes herein, unless otherwise stated, are D50 values, i.e. 50 vol.-% of the particles have a diameter which is smaller than the stated value. Fillers serve primarily to adjust the viscosity, the mechanical and/or the optical properties of the materials.

The surface of the fillers can be modified, for example in order to improve the dispersibility of the fillers in the organic matrix. Those compounds which are chemically bonded, i.e. by ionic or covalent bonds, to the surface of the fillers are preferably used for the surface modification. Compounds which contain either acid groups, preferably carboxylic acid groups, phosphonic acid groups, hydrogen phosphate groups or acid phosphoric acid ester groups, or silyl groups, preferably alkoxysilyl groups, are preferred. The particle surface can be partially or preferably completely covered with the modification agent. The modification agents used according to the invention are monomeric compounds. Linear carboxylic acids, such as e.g. formic acid, acetic acid, propionic acid, octanoic acid, isobutyric acid, isovaleric acid, pivalic acid, or phosphonic acids, e.g. such as methyl-, ethyl-, propyl-, butyl-, hexyl-, octyl- or phenylphosphonic acid, are particularly suitable as surface modification agents. As silyl group-containing compounds, silanes such as propyltrimethoxysilane, phenyltrimethoxysilane, hexyltrimethoxysilane, octyltrimethoxysilane, trimethylchlorosilane, trimethylbromosilane, trimethylmethoxysilane and hexamethyldisilazane are preferred. Quite particularly preferred surface modification agents are acid phosphoric acid esters such as e.g. dimethyl, diethyl, dipropyl, dibutyl, dipentyl, dihexyl, dioctyl or di(2-ethylhexyl) phosphate. The surface modification agents can also comprise radically polymerizable groups, for example (meth)acrylate groups, which react with component (a) and are thus integrated into the polymer network.

Preferred fillers are particulate waxes, in particular carnauba wax, preferably with a particle size of from 1 to 10 µm, cross-linked polymethyl methacrylate (PMMA) particles, preferably with a particle size of from 500 nm to 10 µm, as well as polyamide-12 particles, preferably with a particle size of from 5 to 10 µm. For stereolithography, fillers are preferably used the maximum particle size of which is smaller than the thickness of the stereolithographically produced layers. Particles with a maximum size of 25 µm are preferred, preferably a maximum of 15 µm.

Filler-free materials are preferred according to the invention.

The rheological properties of the materials according to the invention are adapted to the desired intended use. Materials for stereolithographic processing are preferably adjusted such that their viscosity is in the range of from 50 mPa·s to 100 Pa·s, preferably 100 mPa·s to 10 Pa·s, particularly preferably 100 mPa-s to 5 Pa·s. The viscosity is determined at the desired processing temperature of the materials with a cone and plate viscometer (shear rate 100/s). The processing temperature is preferably in the range of from 10 to 70° C., particularly preferably 20 to 30° C.

Materials for manual processing are preferably adjusted such that they have a paste-like consistency.

For the production of highly fluid materials, liquid monomers and highly liquid components (c) are preferably used, whereas for the production of materials with high viscosity, e.g. solid monomers and/or highly viscous or solid components (c) can also be used.

The materials according to the invention can also preferably contain in addition one or more UV absorbers. Preferred UV absorbers are 2,2'-methylenebis[6-(2H-benzotriazol-2-yl)-4-(1,1,3,3-tetramethylbutyl)phenol] (CAS No. 103597-45-1), 2,2',4,4'-tetrahydroxybenzophenone (CAS No. 131-55-5), 2-tert-butyl-6-(5-chloro-2H-benzotriazol-2-yl)-4-methylphenol (CAS No. 3896-11-5), 2,2'-benzene-1, 4-diylbis(4H-3,1-benzoxazin-4-one) (CAS No. 18600-59-4), 2-(4,6-bis-(2,4-dimethylphenyl)-1,3,5-triazin-2-yl)-5-(octyloxy)phenol (CAS No. 2725-22-6), 2-(2-hydroxy-5-methylphenyl)benzotriazole (CAS No. 2440-22-4) and 2-(2H-benzotriazol-2-yl)-6-dodecyl-4-methylphenol (CAS No. 23328-53-2).

Also suitable are so-called Hindered Amine Light Stabilizers such as bis(1,2,2,6,6-pentamethyl-4-piperidyl) sebacate (CAS No. 41556-26-7) and methyl 1,2,2,6,6-pentamethyl-4-piperidyl sebacate (CAS No. 82919-37-7), bis(1-octyloxy-2,2,6,6-tetramethyl-4-piperidyl) sebacate (CAS No. 129757-67-1), bis(1,2,2,6,6-pentamethyl-4-piperidyl) [[3,5-bis(1,1-dimethylethyl)-4-hydroxyphenyl]methyl] butylmalonate (CAS No. 63843-89-0).

In addition to the above-named components, the materials according to the invention can contain one or more further additives, which are preferably selected from thickeners, optical brighteners (e.g. Lumilux LZ Blue, CAS No. 658084-50-5, or 2,5-bis(5-tert-butyl-benzoxazol-2-yl)thiophene, CAS No. 7128-64-5) and, in the case of materials containing fillers, from dispersants.

The materials according to the invention preferably have the following composition:
  20 to 90 wt.-%, preferably 42.5 to 82.5 wt.-%, particularly preferably 50 to 79.3 wt.-% component (a),
  0.1 to 5 wt.-%, preferably 0.3 to 2.5 wt.-%, particularly preferably 0.5 to 1.5 wt.-% (photo)initiator (b) and
  9.9 to 79.9 wt.-%, preferably 15 to 55 wt.-%, particularly preferably 20 to 48.5 wt.-% inert component (c).
  A quite particularly preferred composition contains:
  54.7 to 77.7 wt.-%, preferably 64 to 74 wt.-% component (a), preferably UDMA, TEGDMA, a mixture of UDMA and TEGDMA or a mixture of UDMA, TEGDMA and bis-GMA, 0.5 to 1.5 wt.-%, preferably 0.6 to 1.2 wt.-% (photo) initiator (b) and 23.8 to 44.8 wt.-%, preferably 24.8 to 35.4 wt.-% inert component (c), preferably PPG with a molecular weight of 1000 to 4000 g/mol, particularly preferably 1500 to 3000 g/mol, co-PEG-PPG with a molecular weight of 1000 to 10,000 g/mol, particularly preferably 1500 to 5000 g/mol, quite particularly preferably 2000 to 4000 g/mol and in particular polypropylene glycol with a molecular weight of approx. 2000 g/mol.

Most preferred is a composition, which contains 64 to 74 wt.-% UDMA, TEGDMA, a mixture of UDMA and TEGDMA or a mixture of UDMA, TEGDMA and bis-GMA as component (a), 0.6 to 1.2 wt.-% photoinitiator (b) and 24.8 to 35.4 wt.-% polypropylene glycol (PPG) with a molecular weight of 1000 to 4000 g/mol, particularly preferably 1500 to 3000 g/mol and in particular with a molecular weight of approx. 2000 g/mol as inert component (c).

Furthermore, the materials according to the invention preferably additionally contain:

0.0001 to 1 wt.-%, preferably 0.0001 to 0.5 wt.-%, particularly preferably 0.0001 to 0.2 wt.-% colorant; and/or 0.0001 to 2 wt.-%, preferably 0.0001 to 1 wt.-%, particularly preferably 0.0001 to 0.5 wt.-% UV absorber; and/or 0 to 40 wt.-%, preferably 0 to 30 wt.-%, particularly preferably 1 to 20 wt.-% organic filler.

Moreover, the materials preferably contain 0 to 5 wt.-%, preferably 0 to 3 wt.-%, particularly preferably 0 to 2 wt.-% further additive(s).

Unless otherwise stated, all data relate to the total weight of the material. The individual constituents are preferably selected from the above-named preferred components.

The materials according to the invention are suitable in particular for the production of models for castings made of metal or glass ceramic, in particular for the production of models for dental restoration, such as e.g. inlays, onlays, veneers, crowns, bridges or frameworks as well as removable (partial) prostheses.

A subject of the invention is furthermore a process for the production of dental restorations in which, (A) with a modelling material according to the invention, a model of the tooth to be restored or of the teeth to be restored is moulded, (B) the model is then invested in an investment material, (C) after the investment material has set, the invested model is heated in a furnace until the modelling material is completely removed from the mould, (D) an alloy or a glass ceramic material is poured or pressed into the mould produced in this way.

The production of the model in step (A) preferably takes place by a stereolithographic process. For this purpose, a virtual image of the tooth position is generated on the computer by the direct or indirect digitization of the tooth to be restored or of the teeth to be restored, a model of the dental restoration is then designed on the computer on the basis of this image and this is then produced by additive stereolithographic manufacturing.

In step (B), the model can then be invested in an investment material in a conventional manner. The materials according to the invention are suitable for use with conventional dental investment materials. A distinction is drawn between investment materials containing plaster and those without. Plaster-containing investment materials contain plaster and quartz as main constituents in the ratio 1:2 to 1:4. Plaster serves as a binder. A preferred modification of quartz is cristobalite. Plaster-free investment materials which contain phosphates as binder are preferred. Phosphate-bonded investment materials contain $SiO_2$ modifications which are resistant to high temperatures, and a binder. A mixture of magnesium oxide and ammonium phosphate ($NH_4H_2PO_4$) is preferably used as binder. The mixtures set after mixing with water.

The removal of the model from the mould in step (C) takes place by heating e.g. in a furnace to a temperature of preferably 600° C. to 1000° C. The heating can take place in one or more stages. It is possible but not absolutely necessary to raise the temperature to the desired end temperature in a controlled manner. The mould is then heated further, wherein residual model material is thermally decomposed.

After the investment material has set, the invested model can be placed directly in a furnace which has been preheated to the temperature required for the melting out and/or burn-out of the model. The melting out and/or burn-out typically takes place at a temperature of approx. 850° C. The temperature cycle recommended by the investment material producer is preferably used. Often, the model has already completely burnt or flowed out after an hour. The maximum residence time in the furnace can vary depending on the investment material and the producer. In most cases, it is sufficient to leave the mould in the furnace at the maximum temperature for 1 to 8 hours. The heating-up process can take several hours (1-12 h).

In step (D), a metal alloy is poured or a suitable glass ceramic material is pressed into the negative mould of the original model thus produced. Metal alloys suitable for dental purposes or glass ceramic materials suitable for dental purposes are preferably used.

EMBODIMENT EXAMPLES

Examples 1 to 9

Modelling Materials

The components listed in Table 1 were mixed with each other homogeneously in the stated quantities. The components were weighed out and stirred at approx. 50° C. for 1 hour and then at room temperature for approx. 16 h (overnight). In the case of pigment- and filler-containing compositions, the pigment and the filler respectively were stirred into UDMA, the substances were then homogenized and dispersed three times with a three-roll mill with a gap width of 10 μm and then stirred into the remaining, already dissolved organic matrix (at least 1 hour at room temperature). Finally, optional further additives such as thickeners were added to the paste and stirred again for at least 1 hour.

TABLE 1

Modelling materials for stereolithography

| Component | Composition [wt.-%] | | | | | | | | |
|---|---|---|---|---|---|---|---|---|---|
| | 1 | 2 | 3 | 4 | 5 | 6 | 7 | 8 | 9 |
| Monomer (a) | | | | | | | | | |
| UDMA[1] | 42 | 44 | 49 | 48.95 | 49 | 36.15 | 34 | 49 | 32 |
| TEGDMA[2] | 27 | 25 | 10.04 | 20 | 20 | 20.88 | 17 | 20 | 27 |
| Bis-GMA[3] | — | — | — | — | — | — | — | — | 10 |
| Initiator (b) | | | | | | | | | |
| Irgacure 819[4] | 0.95 | — | — | 0.95 | — | — | — | — | — |
| TPO[5] | — | 0.95 | 0.95 | — | 0.95 | 0.92 | 0.95 | 0.95 | 0.95 |
| Inert component (c) | | | | | | | | | |
| PPG 2000[6] | 30 | 30 | 40 | 30 | 30 | 30 | — | 20 | 30 |
| PPG 1500[7] | — | — | — | — | — | — | 20 | — | — |
| PPG 4000[8] | — | — | — | — | — | — | 8 | — | — |
| PPG 400[9] | — | — | — | — | — | — | — | 10 | — |
| Dye | | | | | | | | | |
| Sudan IV[10] | 0.05 | — | 0.01 | 0.05 | 0.05 | 0.05 | 0.05 | 0.05 | 0.05 |
| Sudan Black B[11] | — | 0.05 | — | — | — | — | — | — | — |
| White pigment (TiO$_2$)[12] | — | — | — | 0.05 | — | — | — | — | — |
| Further components | | | | | | | | | |
| Wax particles[13] | — | — | — | — | — | 10 | — | — | — |
| Thickener[14] | — | — | — | — | — | 2 | — | — | — |
| PMMA particles[15] | — | — | — | — | — | — | — | 20 | — |

[1]Urethane dimethacrylate (CAS No. 72869-86-4)
[2]Triethylene glycol dimethacrylate (CAS No. 109-16-0)
[3]Addition product of methacrylic acid and bisphenol A diglycidyl ether
[4]Phenylbis(2,4,6-trimethylbenzoyl)phosphine oxide (CAS No. 162881-26-7)
[5]Diphenyl(2,4,6-trimethylbenzoyl)phosphine oxide (CAS No. 75980-60-8)
[6]Poly(propylene glycol) (CAS No. 25322-69-4), MW = 2000 g/mol
[7]Poly(propylene glycol) (CAS No. 25322-69-4), MW = 1500 g/mol
[8]Poly(propylene glycol) (CAS No. 25322-69-4), MW = 4000 g/mol
[9]Poly(propylene glycol) (CAS No. 25322-69-4), MW = 400 g/mol
[10]CAS No. 85-83-6
[11]CAS No. 4197-25-5
[12]Titanium dioxide white pigment, particle size D50 <500 nm
[13]MC6015, micronized carnauba wax, d = 1-10 μm
[14]Solution of a high-molecular-weight, urea-modified, medium polar polyamide (Byk 430)
[15]highly cross-linked PMMA, Chemisnow MX80H3wT (Soken Chemical & Engineering Co., Ltd., Japan), D50 = 800 nm

Example 10

Modelling Materials—Comparison Examples

Analogously to Examples 1 to 9, the comparison materials listed in Table 2 were prepared.

TABLE 2

Comparison materials for stereolithography

| Component | Composition [wt.-%] | | |
|---|---|---|---|
| | V1* | V2* | V3* |
| Monomer (a) | | | |
| UDMA[1] | — | 74 | 40 |
| TEGDMA[2] | — | 25 | 25 |
| SR348C[16] | 59 | — | — |
| SR480[17] | 40 | — | — |
| Initiator (b) | | | |
| TPO[5] | 0.95 | 0.9 | 0.95 |
| Inert component (c) | — | — | — |
| Dye | | | |
| Sudan IV[10] | 0.05 | 0.1 | 0.05 |
| Further components | | | |
| Wax particles[13] | — | — | 34 |

*Comparison material
[1-15]see Table 1
[16]Bisphenol A dimethacrylate with 3 ethoxy groups (Sartomer)
[17]Bisphenol A dimethacrylate; ethoxylated 10 times on average

Example 11

Measurement of the Thermal Expansion

For the determination of the thermal expansion of the materials, cylinders with a 6 mm diameter and a height of 6 mm were produced stereolithographically with a printer from the materials described in Tables 1 and 2. The cylinders were cured in layers and then post-exposed in a post-exposure device at a wavelength of 400 nm with an intensity of 10 mW/cm$^2$ for 5 minutes. The cylinders were then placed in the sample chamber of a thermomechanical analyzer (Q400 type from TA Instruments with a macro-expansion probe) and heated at a heating rate of 5 K/min to 800° C. The linear thermal expansion of the cylinders during heating up and the thermal decomposition in the temperature range of from 30° C. to 800° C. was measured in an air atmosphere. The contact force of the measuring probe was 0.1 N.

In FIGS. 1 to 4, the expansion curves for the materials from Examples 2, 4, 5 and 6 are shown. In all cases, the thermal expansion remained significantly below 0.7% over the whole measurement range. The maximum linear thermal expansion was reached in all cases at a temperature below 90° C. Thereafter, the length of the cylinders remained below the maximum value. From 300° C., the materials decomposed thermally and burned out without residue (residue on ignition in all cases <0.1 wt.-%). The decomposition manifests itself in a steep fall in the linear thermal expansion.

Example 6 shows that the wax particles used as filler have practically no influence on the expansion.

The expansion curves of the other examples are similar. In Example 8, the maximum thermal expansion of <1.5% is reached at 125° C.

For comparison, the expansion curves of conventional, commercially available stereolithography materials for the lost-wax technique were determined. FIG. 5 shows the expansion curve of the Bego material VarseoWax CAD/Cast. The material expands by more than 4%, and the temperature of the maximum expansion is only reached shortly before the thermal decomposition, i.e. at more than 300° C.

Figure 6:
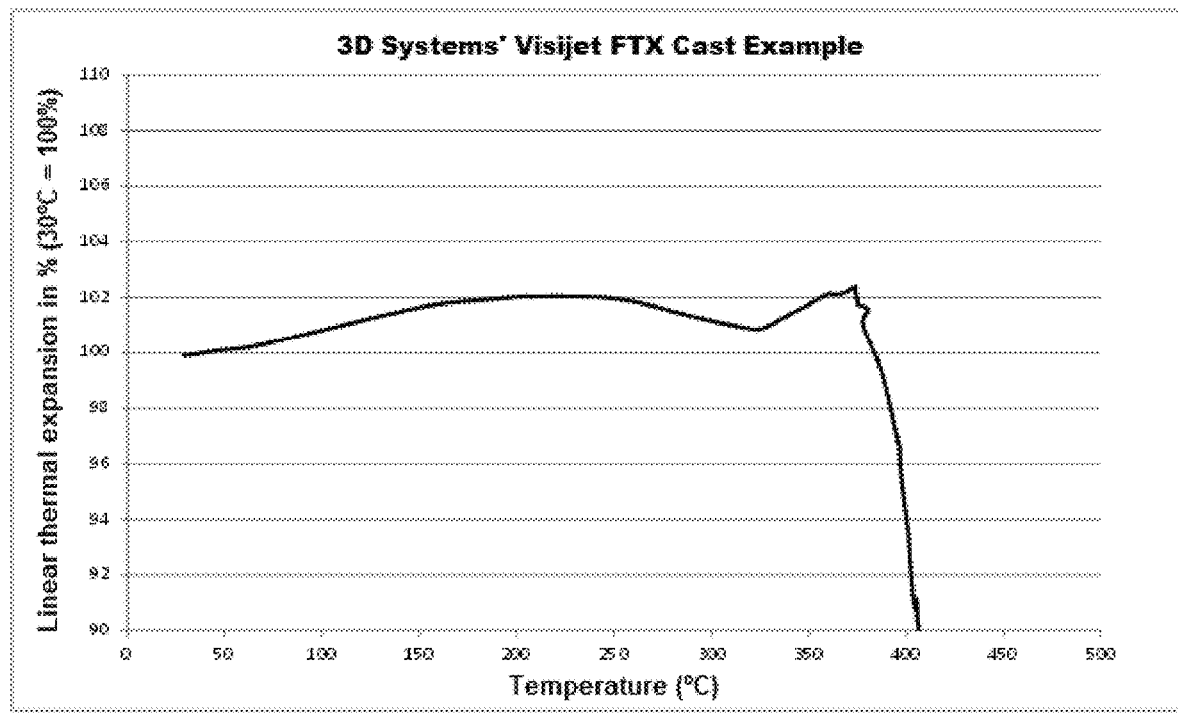

In FIG. 6, the expansion curve is shown of a further stereolithography resin for the lost-wax technique customary in the trade (3D Systems' Visijet FTX Cast). The material expands by more than 2%, and the temperature of the maximum thermal expansion is above 200° C.

Figure 7:
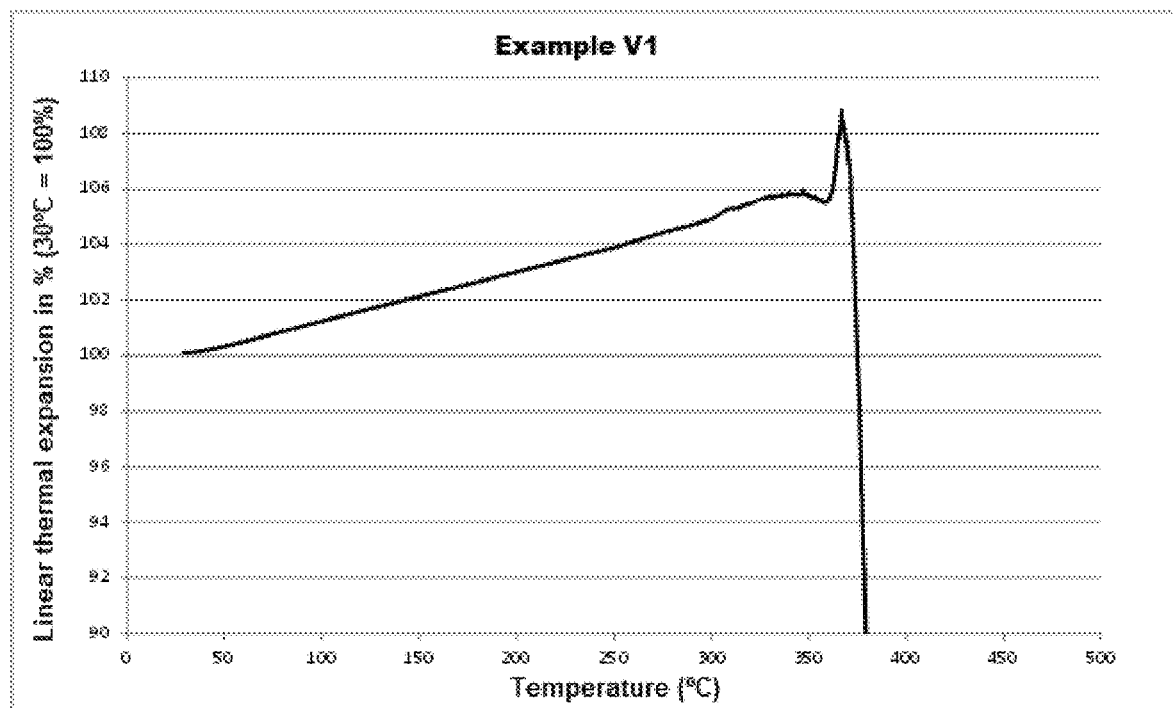
FIGS. 7 and 8 show the thermal expansion curves of comparison materials which do not contain any inert component (c).
Figure 8:
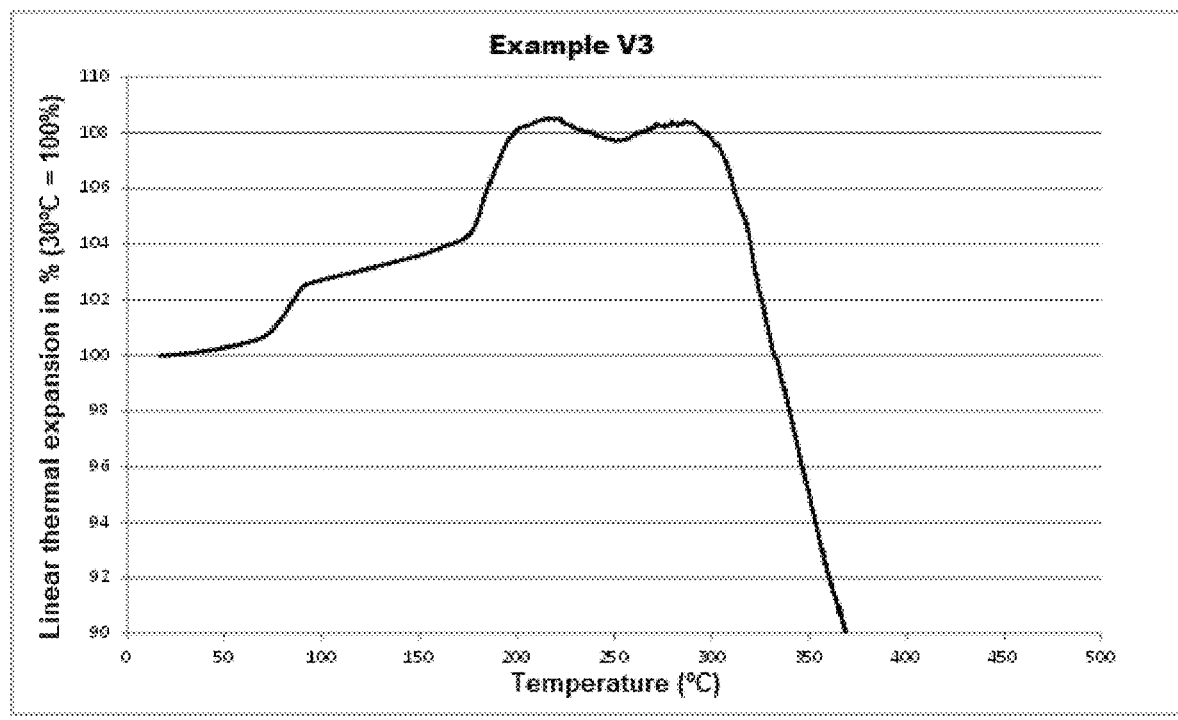

FIGS. 7 and 8 show the expansion curves of comparison materials V1 and V3. Material V1 expands by more than 6% (FIG. 7); material V3 by more than 8% (FIG. 8). In both cases, the temperature of the maximum expansion was only reached shortly before the thermal decomposition, i.e. at more than 300° C. or more than 200° C., respectively.

The measurements show that the maximum thermal expansion of the comparison materials is greater in all cases than that of the materials according to the invention. By adding component (c), the thermal expansion can be effectively reduced. Moreover, in the case of the comparison materials, the maximum linear thermal expansion is at significantly higher temperatures, which are determined by the decomposition temperature of the materials.

Example 12

Production of Models

With a 3D printer, models of a three-unit bridge were manufactured from the materials described in Examples 1 to 9 and with materials customary in the trade. In all cases, the same dataset was used to produce the models.

The models were built up on a ring base with the compatible ring gauge and provided with pressing channels. The models were then invested in each case in a phosphate-based investment material customary in the trade (200 g PressVest Speed; Ivoclar Vivadent AG). The fine investment of the cavities was undertaken with a small brush. The invested ring was allowed to set without vibration for 35 minutes. The rings were then placed directly in the preheating furnace preheated to 850° C. and left there at 850° C. for 1.5 h, in order to remove the models from them completely. The rings were then taken out of the preheating furnace and the hot rings were fitted with a ceramic ingot (IPS e.max Press ingot, Ivoclar Vivadent AG), placed in the hot press furnace (Programat EP 5010, Ivoclar Vivadent) and the chosen press program was started.

After the end of the pressing procedure, the rings were taken out of the furnace and placed on a cooling grid in a place protected from draughts for cooling. After cooling to room temperature, the rings were separated using a separating disc and the pressed objects were divested. The rough divested took place using polishing jet medium at 4 bar pressure, the fine divesting using polishing jet medium at 2 bar pressure. The press results were assessed directly after the fine divesting.

Figure 9:
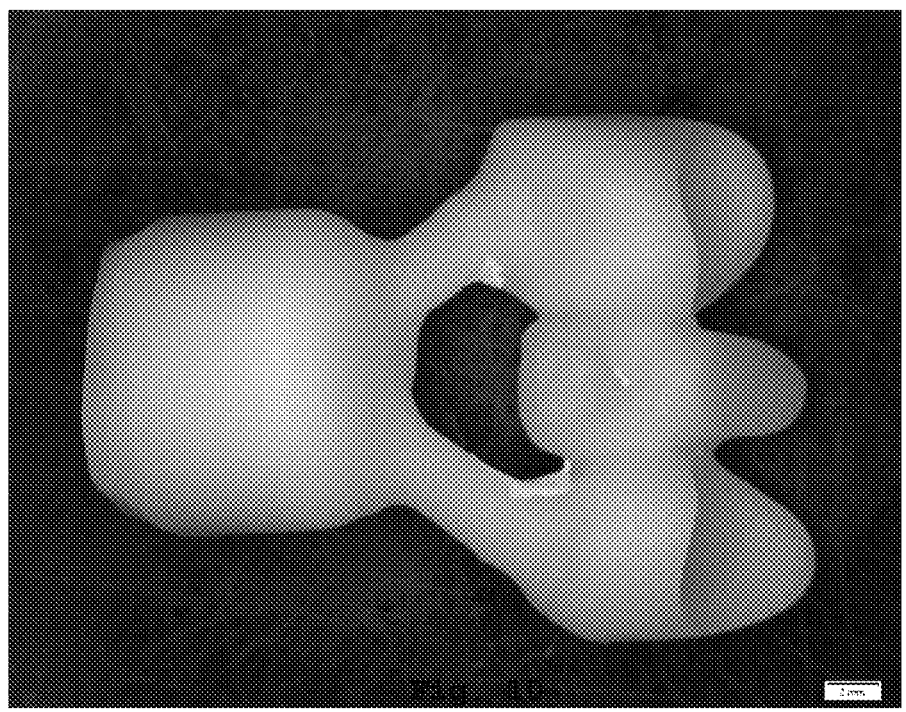
FIGS. 9 to 11 show dental bridge frameworks made of glass ceramic which were produced using the materials according to the invention from Examples 4 (FIG. 9), 5 (FIG. 10) and 8 (FIG. 11), directly after the deflasking. The bridge frameworks do not exhibit any pressing defects.
Figure 10:
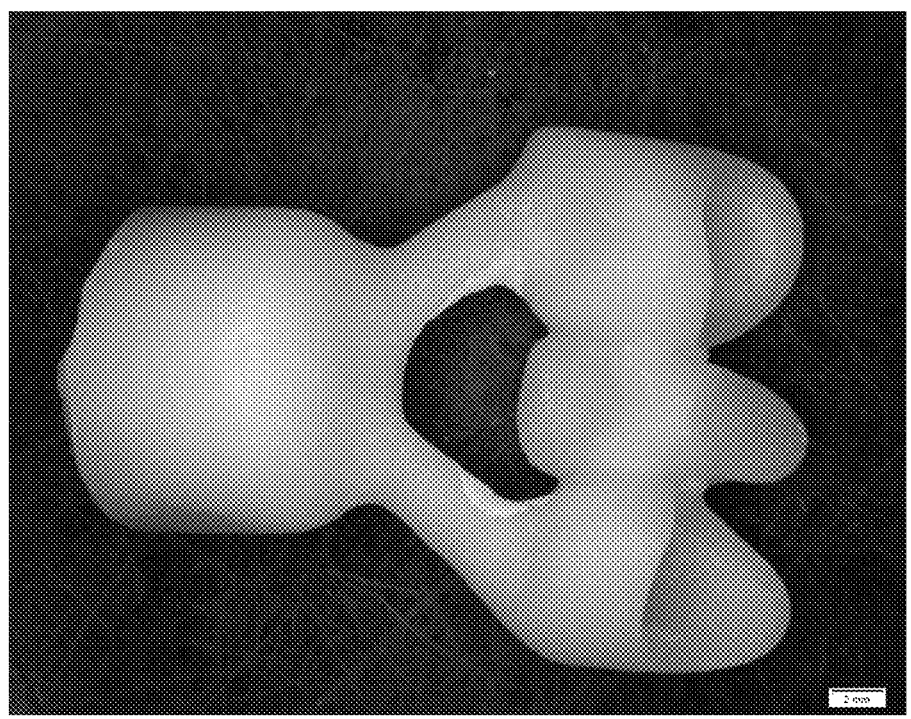
Figure 11:
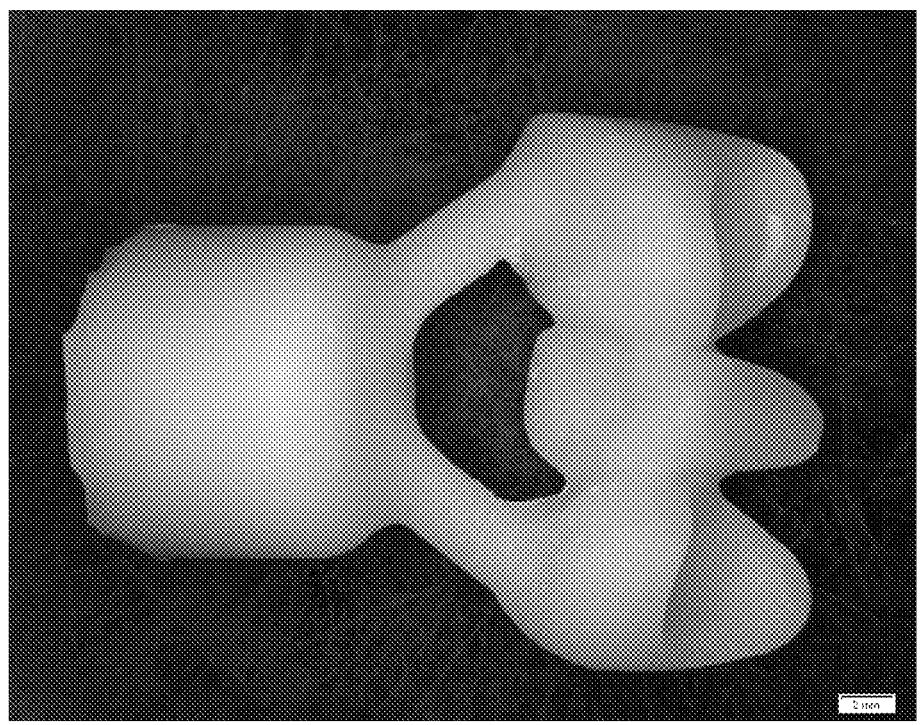

FIGS. 9 to 11 show bridge frameworks by way of example, which were produced using the materials according to the invention from Examples 4, 5 and 8. The pictures were produced directly after the divesting. No pressing defects are visible. The bridges produced with the other materials according to the invention were similar, in no case were pressing defects present.

In contrast thereto, the bridges manufactured using the comparison materials exhibited clearly visible pressing defects, which can be attributed to cracks in the mould which formed during the expansion of the modelling materials.

Figure 12:
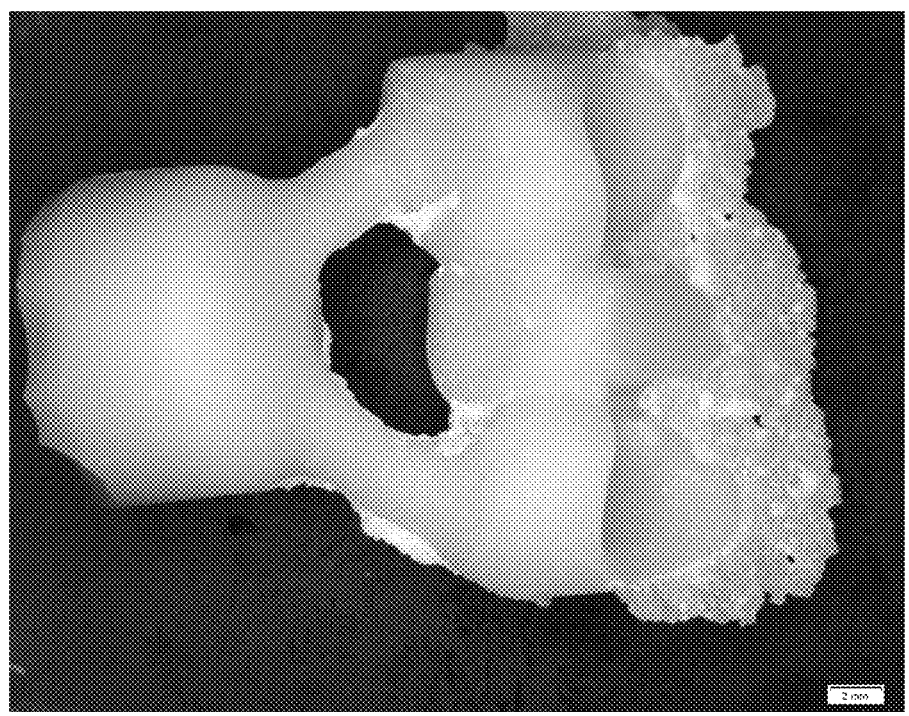
FIGS. 12 to 14 show dental bridge frameworks made of glass ceramic which were produced using comparison materials without component (c) (FIG. 12, material V1.
Figure 13:
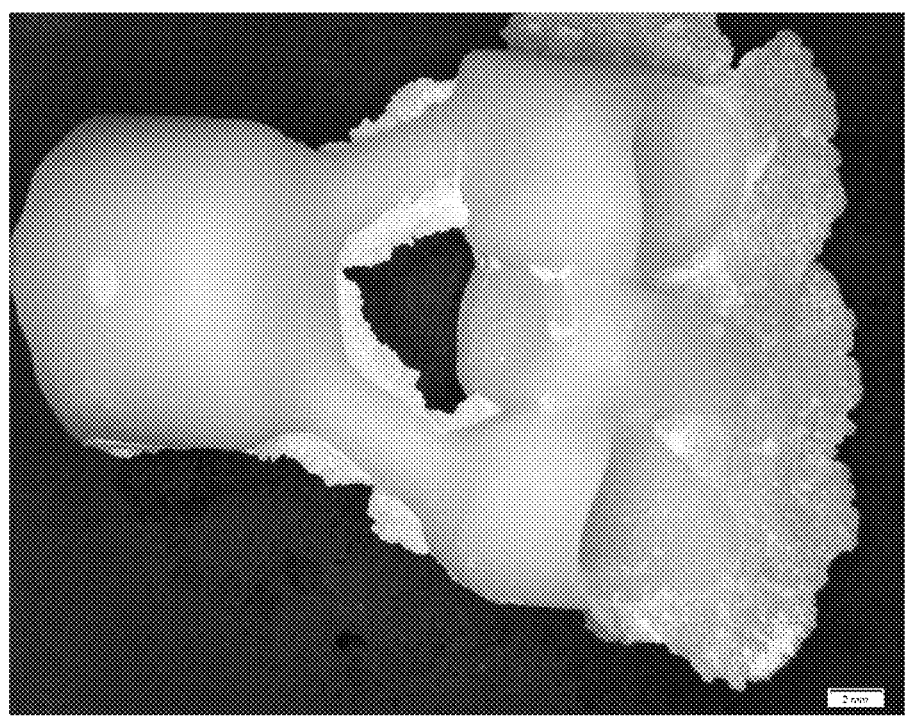
Figure 14:
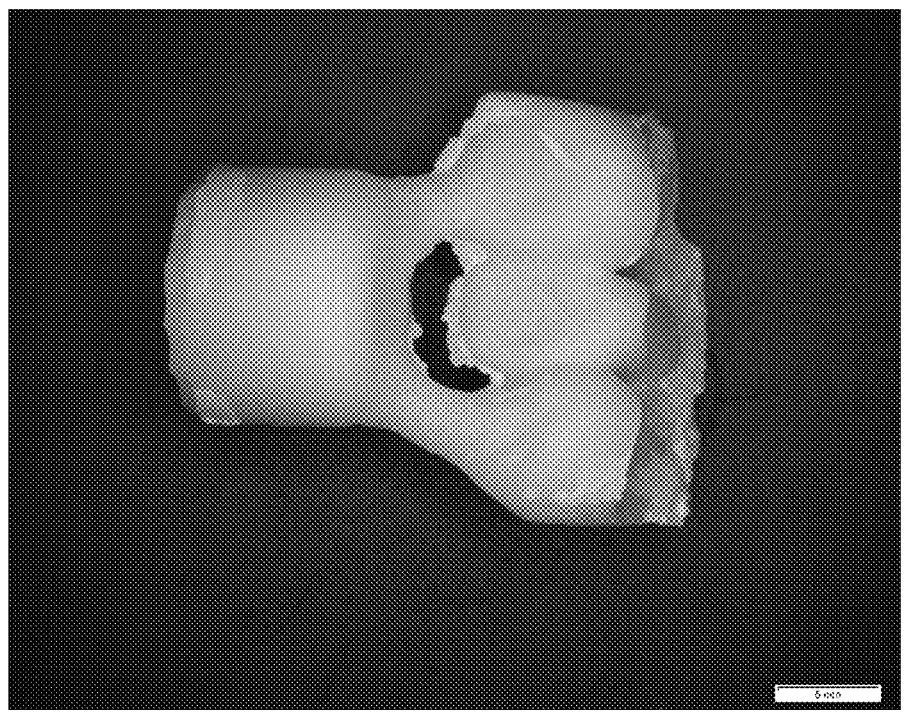
Figure 15:
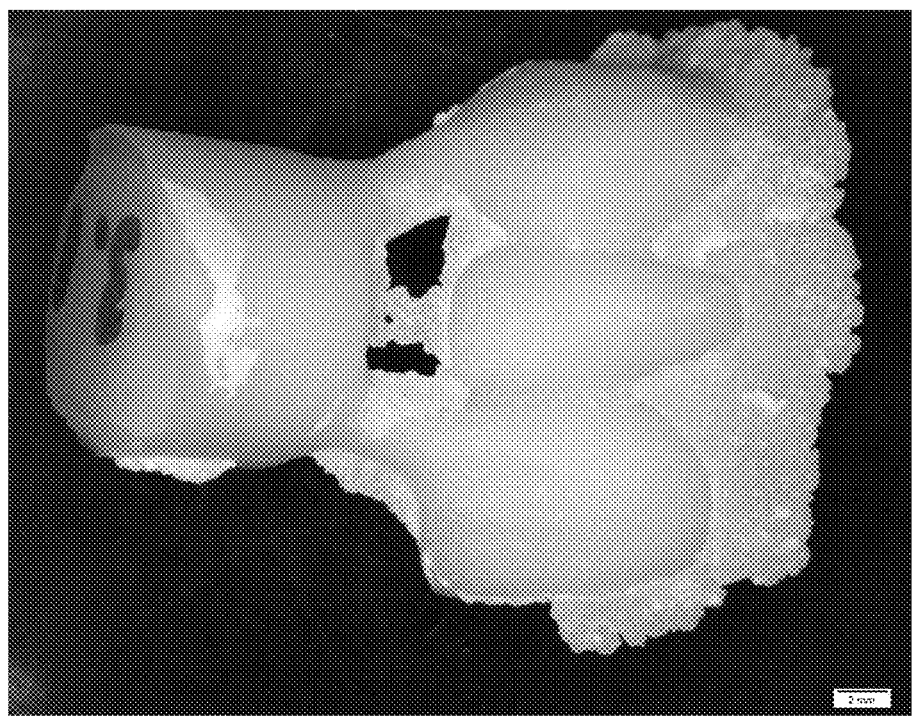
FIGS. 15 and 16 show dental bridge frameworks made of glass ceramic which were produced using materials customary in the trade. The bridge frameworks exhibit clearly visible pressing defects.
Figure 16:
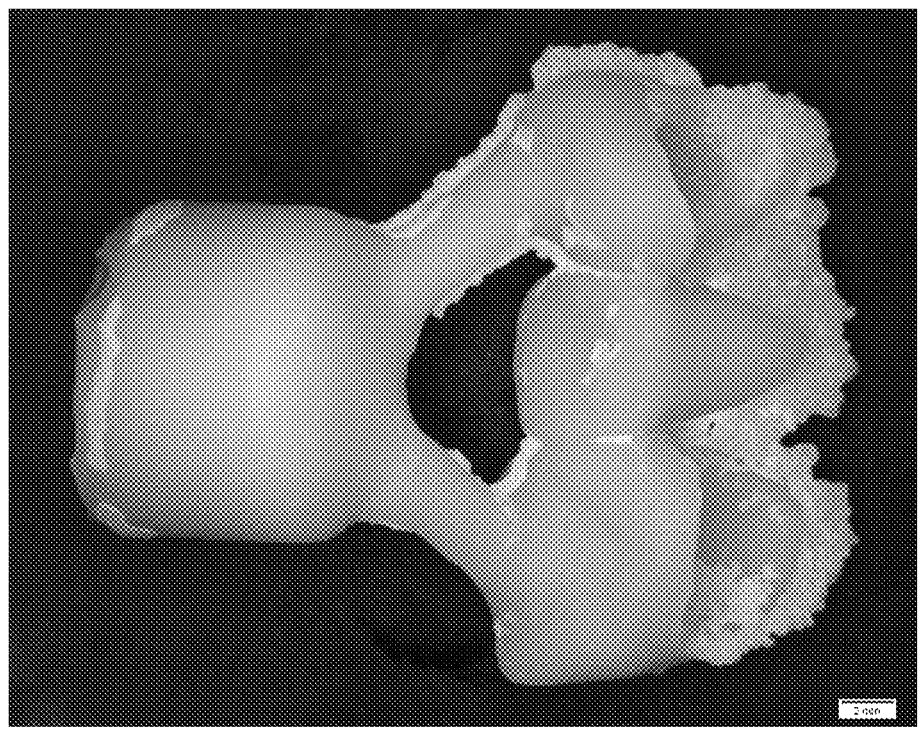

FIGS. 12 to 14 show the bridge frameworks obtained using the comparison materials V1 to V3. FIG. 15 shows a bridge manufactured using the Bego material Varseo Wax CAD/Cast customary in the trade and FIG. 16 shows a bridge manufactured using the 3D Systems product Visijet FTX Cast. In all cases, pressing defects are present, which make a more or less complex finishing of the restorations necessary. Some of the restorations were unusable.

Even the bridge obtained using the 3D Systems product Visijet FTX Cast exhibited pressing defects, although, at approx. 2%, this material has a relatively small maximum thermal expansion. In contrast thereto, the bridge obtained with the material according to the invention from Example 8 (FIG. 11; max. expansion <1.5%) was fault-free. In the case of the material according to the invention, the maximum thermal expansion is reached at 125° C.; in the case of the comparison material only at above 200° C.

The comparison material V3 contained wax particles but no component (c). The model expanded greatly on burn-out; the press results were correspondingly poor.

The invention claimed is:

1. Process for the production of dental restorations in which,
   (A) a model of a tooth to be restored or of teeth to be restored is moulded, wherein the model is fabricated of a radically polymerizable composition which comprises
      (a) at least one radically polymerizable monomer,
      (b) at least one initiator for the radical polymerization and
      (c) at least one inert component, which is selected from phthalates, polyethylene glycols (PEG), polypropylene glycols (PPG), PEG-PPG copolymers, glycerol derivatives, ethoxylated or propoxylated glycerol, ethylenediamine tetrakispropoxylates and ethylenediamine tetrakisethoxylates,
   (B) the model is then invested in an investment material,
   (C) after the investment material has set, the invested model is heated in a furnace so that the modelling material is completely removed from the mould, and
   (D) an alloy or a ceramic or glass ceramic material is poured or pressed into the mould.

2. The process according to claim 1, in which the inert component (c) is selected from
- polyethylene glycols (PEG) with a molecular weight of 1000 to 5000 g/mol,
- polypropylene glycols (PPG) with a molecular weight of 1000 to 4000 g/mol,
- PEG-PPG copolymers with a molecular weight of 1000 to 10,000 g/mol,
- ethylenediamine tetrakispropoxylates and ethylenediamine tetrakisethoxylates with a molecular weight of 1000 to 10,000 g/mol.

3. The process according to claim 1, wherein the composition of step (A) comprises, as component (a), at least one (meth)acrylate and/or (meth)acrylamide or one or more mono-or multifunctional (meth)acrylates or a mixture thereof.

4. The process according to claim 3, wherein the composition of step (A) comprises, as component (a), UDMA, TEGDMA, bis-GMA (addition product of methacrylic acid and bisphenol A diglycidyl ether) or 2-phenoxyethyl acrylate, a mixture of UDMA, TEGDMA and 2-phenoxyethyl acrylate or UDMA, TEGDMA and bis-GMA or a mixture of UDMA and TEGDMA.

5. The process according to claim 4, wherein the composition of step (A) comprises, as component (a), UDMA, TEGDMA or a mixture thereof and at most 20 wt.-% of at least one further monomer, relative to the total mass of component (a).

6. The process according to claim 1, wherein the composition of step (A) comprises, as initiator (b), a photoinitiator.

7. The process according to claim 6, wherein the composition of step (A) comprises, as photoinitiator, benzophenone, benzoin or a derivative thereof, an α-diketone or a derivative thereof, 9,10-phenanthrenequinone, 1-phenylpropane-1,2-dione, diacetyl, 4,4'-dichlorobenzil, camphorquinone (CQ), 2,2-dimethoxy-2-phenyl-acetophenone, an α-diketone in combination with an amine as reducing agent, a Norrish type I photoinitiator, a monoacyl- or bisacylphosphine oxide, a monoacyltrialkyl- or diacyldialkylgermanium compound, benzoyltrimethylgermanium, dibenzoyldiethylgermanium, bis(4-methoxybenzoyl)diethylgermanium (MBDEGe), a mixture of bis(4-methoxybenzoyl)diethylgermanium in combination with camphorquinone and 4-dimethylaminobenzoic acid ethyl ester, camphorquinone (CAS No. 10373-78-1) in combination with ethyl 4-(dimethylamino)benzoate (EMBO, CAS No. 10287-53-3), 2,4,6-trimethylbenzoyl diphenylphosphine oxide (TPO, CAS No. 75980-60-8), ethyl (2,4,6-trimethylbenzoyl) phenylphosphinate (TPO-L, CAS No. 84434-11-7), phenyl-bis(2,4,6-trimethylbenzoyl)phosphine oxide (CAS 162881-26-7), bis(2,6-difluoro-3-(1-hydropyrrol-1-yl)phenyl)titanocene (CAS No. 125051-32-3), 2-benzyl-2-(dimethylamino)-4'-morpholinobutyrophenone (CAS No. 119313-12-1), and/or 1-butanone, 2-(dimethylamino)-2-(4-methylphenyl)methyl-1-4-(4-morpholinyl)phenyl (CAS No. 119344-86-4).

8. The process according to claim 1, wherein the composition of step (A) additionally comprises at least one colorant and/or one inhibitor.

9. The process according to claim 1, wherein the composition of step (A) comprises
- 20 to 90 wt.-% component (a),
- 0.1 to 5 wt.-% (photo)initiator (b) and
- 9.9 to 79.9 wt.-% inert component (c),
in each case relative to the total mass of the composition.

10. The process according to claim 9, wherein the composition of step (A) comprises
- 54.7 to 77.7 wt.-% component (a) comprising UDMA, TEGDMA, a mixture of UDMA and TEGDMA or a mixture of UDMA, TEGDMA and bis-GMA,
- 0.5 to 1.5 wt.-% (photo)initiator (b) and
- 23.8 to 44.8 wt.-% inert component (c) comprising PPG with a molecular weight of 1000 to 4000 g/mol, or co-PEG-PPG with a molecular weight of 1000 to 10,000 g/mol,
in each case relative to the total mass of the composition.

11. The process according to claim 10, wherein the composition of step (A) comprises
- 64 to 74 wt.-% UDMA, TEGDMA, a mixture of UDMA and TEGDMA or a mixture of UDMA, TEGDMA and bis-GMA as component (a),
- 0.6 to 1.2 wt.-% photoinitiator (b) and
- 24.8 to 35.4 wt.-% polypropylene glycol (PPG) with a molecular weight of 1000 to 4000 g/mol as inert component (c),
in each case relative to the total mass of the composition.

12. The process according to claim 9, wherein the composition of step (A) additionally comprises
- 0.0001 to 1 wt.-% colorant; and/or
- 0.0001 to 2 wt.-% UV absorber; and/or
- 0 to 40 wt.-% organic filler; and/or
- 0 to 5 wt.-% further additive(s),
in each case relative to the total mass of the composition.

13. The process according to claim 1, wherein the composition of step (A) has a maximum linear thermal expansion below 1.5%.

14. The process according to claim 13, in which the maximum linear thermal expansion is reached at a temperature of below 150° C.

15. The process according to claim 1, in which the model is produced in step (A) by stereolithography.

16. The process according to claim 1, in which the dental restoration is an inlay, onlay, veneer, a crown, bridge, a framework or a removable (partial) prosthesis.

17. The process according to claim 1, in which the inert component (c) is selected from
- polyethylene glycols (PEG) with a molecular weight of 1000 to 3000 g/mol,
- polypropylene glycols (PPG) with a molecular weight of 1500 to 3000 g/mol,
- PEG-PPG copolymers with a molecular weight of 1500 to 5000 g/mol,
- ethylenediamine tetrakispropoxylates and ethylenediamine tetrakisethoxylates with a molecular weight of 1000 to 5000 g/mol.

18. The process according to claim 1, wherein the composition of step (A) comprises
- 50 to 79.3 wt.-% component (a),
- 0.5 to 1.5 wt.-% (photo)initiator (b) and
- 20 to 48.5 wt.-% inert component (c),
in each case relative to the total mass of the composition.

19. The process according to claim 9, wherein the composition of step (A) comprises
- 64 to 74 wt.-% UDMA, TEGDMA, a mixture of UDMA and TEGDMA or a mixture of UDMA, TEGDMA and bis-GMA as component (a),
- 0.6 to 1.2 wt.-% photoinitiator (b) and
- 24.8 to 35.4 wt.-% polypropylene glycol (PPG) with a molecular weight of 1500 to 3000 g/mol as inert component (c),
in each case relative to the total mass of the composition.

20. The process according to claim 9, wherein the composition of step (A) additionally comprises
   0.0001 to 0.5 wt.-% colorant; and/or
   0.0001 to 1 wt.-% UV absorber; and/or
   0 to 30 wt.-% organic filler; and/or
   0 to 3 wt.-% further additive(s),
in each case relative to the total mass of the composition.

\* \* \* \* \*